United States Patent [19]

Lerch et al.

[11] Patent Number: 5,478,752
[45] Date of Patent: Dec. 26, 1995

[54] ANALYTICAL METHOD AND DEVICE CONTAINING A FLEECE LAYER

[75] Inventors: Rolf Lerch, Ilvesheim; Heinz Macho, Fuerth-Fahrenbach, both of Germany

[73] Assignee: Boehringer Mannheim GmbH, Mannheim, Germany

[21] Appl. No.: 237,410

[22] Filed: May 3, 1994

Related U.S. Application Data

[63] Continuation of Ser. No. 69,342, May 28, 1993, abandoned.

[30] Foreign Application Priority Data

May 29, 1992 [DE] Germany .......................... 42 17 732.4

[51] Int. Cl.⁶ .................................................. G01N 21/00
[52] U.S. Cl. ................. 436/169; 422/56; 422/57
[58] Field of Search ................... 422/56, 57, 58; 436/169, 164

[56] References Cited

U.S. PATENT DOCUMENTS

| | | | |
|---|---|---|---|
| 4,178,277 | 12/1979 | Gebauer et al. | 260/40 R |
| 4,477,575 | 10/1984 | Vogel et al. | 436/170 |
| 4,708,985 | 11/1987 | Diamantoglou et al. | 525/166 |
| 4,912,147 | 3/1990 | Pfoehler et al. | 524/460 |

FOREIGN PATENT DOCUMENTS

| | | |
|---|---|---|
| 0045476 | 2/1982 | European Pat. Off. . |
| 0209032 | 1/1987 | European Pat. Off. . |
| 0297390 | 1/1989 | European Pat. Off. . |
| 0423784 | 4/1991 | European Pat. Off. . |
| 0443231 | 8/1991 | European Pat. Off. . |

*Primary Examiner*—Jeffrey R. Snay
*Attorney, Agent, or Firm*—Nikaido, Marmelstein, Murray & Oram

[57] ABSTRACT

An analytical device is used for the determination of an analyte in a liquid sample. The device includes a fleece layer including fleece material and polyester fibers, and a reagent for determining an analyte. The reagent is for entering into a detectable reaction with the analyte. The polyester fibers are heat-meltable copolyester fibers containing terephthalic acid, isophthalic acid, and 1,4-butanediol.

15 Claims, 1 Drawing Sheet

ANALYTICAL METHOD AND DEVICE CONTAINING A FLEECE LAYER

This application is a continuation of application Ser. No. 08/069,342 filed May 28, 1993, now abandoned.

The present invention concerns an analytical device in form of a so-called test carrier for the determination of an analyte in liquid samples which contains 1) a fleece layer with a portion of polyester fibres and 2) the reagent for the determination of an analyte which enters into a detectable reaction in the presence of the analyte and also concerns a method for the determination of an analyte using this test carrier. In addition the invention concerns a fleece which contains fibres of copolyester containing terephthalic acid, isophthalic acid and 1,4-butanediol as well as the use of fibres made of copolyester containing terephthalic acid, isophthalic acid and 1,4-butanediol for the production of a test carrier or for producing a fleece.

A fleece is a flat structure of disordered loose fibres lying side by side. In contrast the fibres in fabrics or knitted fabrics are arranged regularly and with a defined orientation. Whereas the fibres in fabrics and knitted fabrics are arranged and interact with each other in such a way that these structures already have a high intrinsic coherence even without special auxiliary agents, it is known from the textile industry that fleeces can be strengthened with hot-setting adhesive fibres in order to obtain textile structures which are more stable. Copolyester hot-setting adhesive fibres from the Ems-Grilon S.A. Company., Domat/Ems, Switzerland are known to be suitable for this. A use for these fibres outside the textile industry is not known.

Test carriers are analytical devices in which the reagents necessary for carrying out the determination of a component of a liquid sample are present in or on solid materials which are usually in the form of layers. In general such carrier materials can be absorbent, fibrous or porous materials or materials capable of swelling. The use of fleeces as carrier materials in a layered structure in test carriers is known from the state of the art.

Test carriers with layers of fleece material are for example described in EP-B 0 209 032, EP-A 0 443 231 or EP-A 0 045 476.

Test carriers are disclosed in EP-B 0 209 032 and EP-A 0 443 231 in which a fleece represents one of several layers. Nothing is known from these documents about admixing meltable fibres with non-meltable supporting fibres which represent the backbone of the fleece.

The use of glass fibre fleeces in test carriers to separate erythrocytes from whole blood is described in EP-A 0 045 476. The possibility of admixing heat deformable plastic fibres is mentioned in order to improve the coherence of the glass fibres. Polyester fibres are mentioned in general. Special polyester fibres are not mentioned. Furthermore this application discloses that reagents which prevent haemolysis of erythrocytes, which inhibit or support coagulation or which are necessary in the indicator layer but are not compatible with the reagents located there, can be present in or on the glass fibre fleece.

In test carriers for the determination of analytes in liquid samples which contain fleece materials, one of the functions of such fleeces is to uniformly distribute liquid and substances dissolved therein in the carrier material. However, substances dissolved in the liquid are often not uniformly distributed within the fleece. This can be explained by the fact that when applying a liquid and substances dissolved therein onto a dry fleece the liquid spreads radially from the site of application but the dissolved substances depending on their affinity to the fleece material, migrate at different rates so that concentration gradients of the substances dissolved in the liquid are formed within the moistened fleece material. To illustrate this fact it is often denoted "chromatography effect". When the analyte to be determined is not distributed uniformly within such layers this often also results in variations in the quantitative result for the analyte to be determined depending on where and how the measurement is carried out.

The object of the present invention was to avoid chromatography effects within fleece layers as far as possible.

This object is achieved by the present invention as characterized by the patent claims.

The present invention concerns an analytical device in form of a test carrier for the determination of an analyte in liquid samples which contains 1) a fleece layer with a portion of polyester fibres and 2) a reagent for the determination of an analyte which enters into a detectable reaction in the presence of the analyte which is characterized in that the polyester fibres are meltable by heat and are fibres made of copolyester containing terephthalic acid, isophthalic acid and 1,4-butanediol.

In addition the present invention concerns a fleece which contains fibres made of copolyester containing terephthalic acid, isophthalic acid and 1,4-butanediol which is characterized in that it contains a reagent for the determination of an analyte which enters into a detectable reaction in the presence of the analyte.

In this respect the present invention also concerns the use of fibres made of copolyester containing terephthalic acid, isophthalic acid and 1,4-butanediol for the production of a test carrier according to the present invention or fleece according to the present invention.

Finally the present invention concerns a method for the determination of an analyte in liquid samples in which a test carrier containing 1) a fleece layer which has a portion of polyester fibres and 2) a reagent which enters into a detectable reaction in the presence of the analyte to be determined, is contacted with the liquid sample to be examined and subsequently a detectable reaction is measured as a measure for the type and/or amount of analyte which is characterized in that the fleece layer contains fibres made of copolyester containing terephthalic acid, isophthalic acid and 1,4-butanediol.

Surprisingly it was found that the object set forth above can be achieved by using those fleece materials in test carriers which also contain a portion of heat-deformable polyester fibres in addition to the supporting fibres wherein fibres made of copolyester containing terephthalic acid, isophthalic acid and 1,4-butandediol are used as the heat-deformable polyester fibres. These fibres melt rapidly and only have a low heat shrinkage (preferably less than 20 %). The melting range of fibres made of copolyester containing terephthalic acid, isophthalic acid and 1,4-butanediol is about 100°–220° C., preferably ca. 140°– 200° C. and particularly preferably ca. 160°–180° C. depending on the relative proportions of the monomer components.

The proportion of fibres made of copolyester containing terephthalic acid, isophthalic acid and 1,4-butanediol according to the present invention is about 10–60% by weight, preferably 30–50% by weight in relation to the weight of the total amount of fibres. Meltable copolyester fibres with a titre between 4 and 6 dtex, particularly preferably between 4.1 and 5.5 dtex, have proven to be especially preferable for the present invention whereby this titre is a measure of the diameter of the fibres when the density is known.

All conceivable fibres which do not melt at temperatures up to 230° C. can be used as supporting fibres which represent the backbone of the fleece according to the present invention. Fibres of glass, polyester, polyamide, cellulose or cellulose derivatives as well as mixtures of such fibres which fulfil these requirements are preferred fibres according to the present invention. Supporting fibres of polyester or glass which are difficultly meltable are especially preferred.

In the simplest case a test carrier in a layered form according to the present invention only contains one layer. This then consists of a fleece with supporting fibres and a portion of fibres made of copolyester containing terephthalic acid, isophthalic acid and 1,4-butanediol and in addition contains the reagent necessary for determining an analyte which enters into a detectable reaction in the presence of the analyte whereby a detectable reaction is understood as one in which a signal is generated in the presence of the analyte which can be measured and which represents a measure for the amount or for the type of analyte. Colorimetric or fluorimetric measurement methods are usually used as detection methods. Methods in which the formation, change or decrease in colour is observed are particularly preferred.

The reagent can be uniformly distributed in the fleece of the test carrier according to the present invention, as for example results by impregnating the fleece with the reagent in liquid form. However, it can also be coated on the fleece. In addition the reagent can be immobilized on the fibres of the fleece or be applied in such a way that it can be detached by liquid.

Since fleeces themselves are often not rigid enough to be easily handled when determining an analyte in liquid, a fleece containing reagent according to the present invention can also be mounted on an inert rigid material which facilitates the intended handling of the fleece. Rigid plastic foils have proven to be particularly suitable for this, however, other rigid materials such as glass, metal etc. are also conceivable.

In principle the fleece according to the present invention can be used in all test carriers instead of the fleeces usually used. The fleece according to the present invention can for example be used in test carriers according to EP-A 0 045 476, EP-B 0 209 032 or according to EP-A 0 443 231. In such test carriers the fleece does not have to contain a reagent for determining the analyte since, instead of as an indicator layer, it can also fulfil other functions there such as for example separation of erythrocytes from whole blood, transport of sample liquid between two other layers or zones of a test carrier or even simply as a suction layer for the removal of excess liquid from a certain area of the test carrier. The subject matter of the present analytical device claims is also intended to encompass test carriers with several layers in which the reagent is not present in or on the fleece according to the present invention but on a further layer which can be a fleece but also any other material in a layer form.

There is no general limitation on the type of liquid samples which can be examined with a test carrier according to the present invention. However, it is obvious that the fleece material should be inert with regard to the sample to be examined. Test carriers are usually intended for examining body fluids such as for example blood, serum, plasma, urine, saliva etc. The test carrier according to the present invention is also particularly suitable for examining blood, plasma, serum and urine samples. However, it can also be used to examine other liquids.

In order to carry out the method of determination the test carrier according to the present invention is brought into contact with the liquid sample to be examined, for example by immersion in the liquid to be examined or by applying the liquid to be examined onto the test carrier, and subsequently a detectable reaction is measured as a measure for the type and/or amount of the analyte.

A feature of the fleece according to the present invention is that almost no chromatography effect occurs. In addition the rate at which the liquid spreads in the fleece according to the present invention is considerably higher than in fleeces which contain the usual polyester fibres. These properties enable methods of determination to be carried out more rapidly and more accurately using the fleece according to the present invention.

EXAMPLE 1

Four fleeces (a–d) are produced.

The following serve as starting materials:

a) 30 parts polyester fibres 1.7/6 (Du Pont, Bad Homburg, Germany)

20 parts viscose fibres, 1.7/6 (Rohtex Textil, Mönchengladbach, Germany)

30 parts Grilene fibres (Ems-Grilon S.A., Domat/Ems, Switzerland)

20 parts Kuralon (polyvinylalcohol), (Rohtex Textil, Mönchengladbach, Germany)

b) 60parts polyester fibres 1.7/6 (Du Pont, Bad Homburg, Germany)

20 parts viscose fibres, 1.7/6 (Rohtex Textil, Mönchengladbach, Germany)

20 parts Kuralon (polyvinylalcohol), (Rohtex Textil, Mönchengladbach, Germany)

c) 50 parts glass fibres, type 108, (John Mansfield, Denver, Colorado, U.S.A.)

50 parts Grilene fibres, 1.7/6 (Ems-Grilon S.A., Domat/Ems, Switzerland)

10 parts Kuralon (polyvinylalcohol), (Rohtex Textil, Mönchengladbach, Germany)

d) 100 parts glass fibres type 108, (John Mansfield, Denver, Colorado, U.S.A.)

10 parts Kuralon (polyvinylalcohol), (Rohtex Textil, Mönchengladbach, Germany)

The stated parts are parts by weight.

The Grilene fibres used for fleeces a) and c) are fibres made of copolyester containing terephthalic acid, isophthalic acid and 1,4-butanediol which in this case are used according to the present invention.

A slanted screen machine was used as the paper machine (Voith, Heidenheim, Germany). The fibres suspended in water were pumped onto a slanted screen. While the liquid flows off or is sucked off by a vacuum, the fibres orientate on the surface of the screen and are dried as a fleece by means of a drying cylinder. They are dried at 125° C. until a final humidity of 0.5 to 1.5 by weight is obtained. A suction and production rate of 2 ml per minute are selected so that a material with an area weight of 60 g/m² is produced.

EXAMPLE 2

The fleeces a) to d) produced according to example 1 were cut into strips having a width of 15 mm and a length of 200 mm. 50 µl of a concentrated patent blue solution was pipetted onto one end of the fleece strip and subsequently dried at 60° C.

After drying of the impregnated ends the strips were immersed to a depth of 5 mm in a waterbath and the fleeces were removed from the water after an absorption height of 30 mm had been reached. The washing out and migration properties of the dye were determined visually.

Whereas the fleece samples without Grilene (fleeces b and d) show a distinct colour front and the colour is concentrated at the flow front these effects are much less pronounced in fleece samples containing Grilene (fleeces a and c). In contrast the fleeces containing Grilene fibres are coloured homogeneously over the entire flow area. Concentrations of colour at the flow front are not detectable.

BRIEF DESCRIPTION OF THE DRAWINGS

FIG. 1 shows a fleece (1) consisting of a fleece material (2) which comprises copolyester fibres (3) made of terephthalic acid, isophthalic acid and 1,4-butanediol alone or in admixture with other components. Reagent (4) is uniformly distributed in the fleece material (2).

In FIG. 2 is shown another embodiment of the invention wherein reagent (4) is coated directly upon the fleece material (2).

FIG. 3 depicts an analytical device according to the invention. Fleece material (2) with reagent (4) uniformly distributed therein is provided on a rigid support (5). This support (5) may serve as a handle. When using such a device for a determination of an analyte in a liquid sample support (5) can be held with thumb and index finger, e.g. at position (6). The liquid sample to be examined may then be added onto fleece material (2) or fleece material (2) may also be dipped into the sample. A detectable reaction, e.g. a color development or color change may subsequently be observed on and in the fleece material (2) when the analyte to be determined is present in the sample liquid. If the support (5) is made of transparent material the detectable reaction may also be observed through the support otherwise the detectable reaction may only be measured from a surface of the fleece material (2) which is not fixed to the support (5).

In FIG. 4 there is shown a multilayer analytical device with fleece materials (2,7) according to the invention fixed on a rigid support (5). Reagent (4) is coated onto fleece material (2). Reagent (8) is uniformly distributed in fleece material (7). Such an embodiment may be useful e.g. when the two reagents would not be stable when mixed together. When liquid sample is applied onto fleece material (7) reagent (8) may react with analyte present in the sample to be determined to give a first soluble reaction product. Liquid in fleece material (7) will be drawn by capillary forces into fleece material (2) and the first soluble reaction product will reach this second fleece material (2) together with this liquid. There the first reaction product contacts reagent (4) and give detectable reaction product which may be detected on a surface of fleece material (2) which is not fixed to support (5) or if support (5) is transparent then the detectable reaction product may also be observed through support (5).

Figure 1:
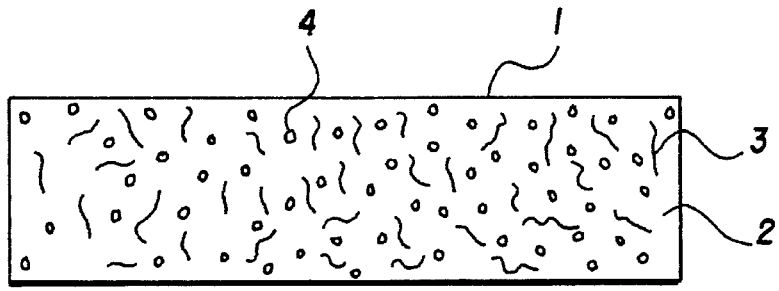
FIG. 1 to 4 show schematic cross-sections through embodiments of analytical devices according to the invention.
Figure 2:
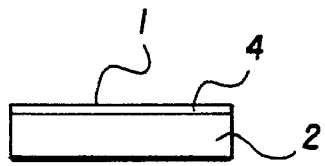
Figure 3:
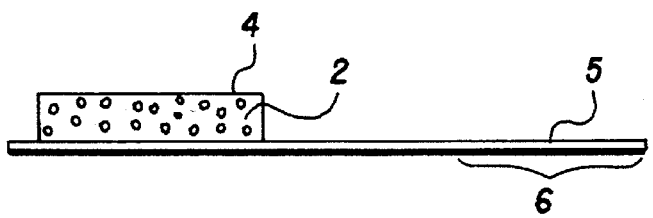
Figure 4:
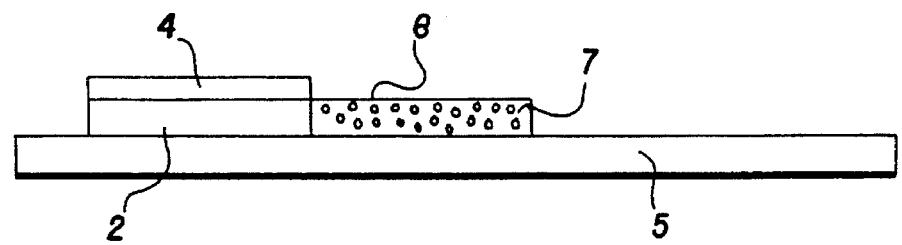

The following references are hereby incorporated by reference:

EP-B-0 209 032

EP-A-0 443 231

EP-A-0 045 476.

We claim:

1. An analytical device for the determination of an analyte in a liquid sample, said analytical device comprising:

a fleece layer including fleece material and polyester fibers; and a reagent for determining an analyte, by entering into a detectable reaction with the analyte;

wherein the fleece material is not heat meltable and the polyester fibers are heat-meltable, and are copolyester fibers containing terephthalic acid, isophthalic acid and 1,4-butanediol.

2. An analytical device as recited in claim 1, wherein said fleece material includes at least one of the group consisting of glass fibers, polyester fibers, polyamide fibers, cellulose fibers, and cellulose derivative fibers, wherein said fibers of said fleece material have melting temperatures above 230° C.

3. An analytical device as recited in claim 1, wherein said fleece layer and said reagent are disposed on an inert rigid material to facilitate handling thereof.

4. An analytical device as recited in claim 1, wherein a titre of said copolyester fibers is between 4 and 6 dtex.

5. An analytical device as recited in claim 1, wherein said reagent is dispersed within said fleece layer.

6. An analytical device as recited in claim 1, wherein the proportion of said meltable polyester fibers to the fleece layer is 10%–60% by weight.

7. An analytical device as recited in claim 6, wherein said polyester fibers form between 30 and 50% of said fleece layer.

8. An analytical device as recited in claim 1, wherein said polyester fibers have a melting point of between 100° C. and 220° C.

9. An analytical device as recited in claim 8, wherein said polyester fibers have a melting point of between 140° C. and 200° C.

10. A method for the determination of an analyte in a liquid sample, comprising the steps of:

providing an analytical device comprising:

a fleece layer including fleece material and polyester fibers; and a reagent for determining an analyte, said reagent being capable of entering into a detectable reaction in the presence of the analyte;

wherein the fleece material is not heat meltable and the polyester fibers are heat-meltable, and are copolyester fibers containing terephthalic acid, isophthalic acid and 1,4-butanediol;

contacting said fleece layer with said liquid sample; and measuring the detectable reaction which occurs as a result of said contacting step to determine at least one of the type and the amount of the analyte.

11. A method of manufacturing an analytical device, comprising the steps of:

forming a fleece layer having fleece material which is not heat meltable and heat-meltable fibers of copolyester containing terephthalic acid, isophthalic acid, and 1,4-butanediol;

impregnating said fleece layer with a reagent for the determination of an analyte, said reagent being capable of entering into a detectable reaction in the presence of the analyte.

12. A method of manufacturing an analytical device as recited in claim 11, further comprising the steps of:

providing an inert rigid material and attaching said fleece layer to said inert rigid material.

13. A method of manufacturing an analytical device, comprising the steps of:

forming a fleece layer having fleece material which is not heat meltable and heat-meltable fibers of copolyester containing terephthalic acid, isophthalic acid, and 1,4-butanediol; and disposing a reagent on an upper surface of said fleece layer, said reagent being for the determination of an analyte and capable of entering into a detectable reaction in the presence of the analyte.

14. A method of manufacturing an analytical device as recited in claim 13, further comprising the steps of:

providing an inert rigid material and attaching said fleece layer to said inert rigid material.

15. An analytical device for the determination of an analyte in a liquid sample, said analytical device comprising:

a fleece layer comprising copolyester fibers having a melting point between 100° C. and 220° C. and containing residues of terephthalic acid, isophthalic acid, and 1,4-butanediol, said fleece layer also having at least one supporting fiber which has a melting point of above 230° C.; and a reagent, said reagent being capable of entering into a detectable reaction in the presence of the analyte.

* * * * *